United States Patent [19]

Carroll

[11] Patent Number: 5,000,776

[45] Date of Patent: Mar. 19, 1991

[54] PROCESS FOR PROTECTING PLANTS AND TREES FROM OZONE DAMAGE

[75] Inventor: Vincent J. Carroll, Williston Park, N.Y.

[73] Assignee: Pfizer Inc., New York, N.Y.

[21] Appl. No.: 172,036

[22] Filed: Mar. 24, 1988

[51] Int. Cl.$^5$ ............................................. A01N 43/08
[52] U.S. Cl. ......................................................... 71/88
[58] Field of Search ............................................. 71/88

[56] References Cited

U.S. PATENT DOCUMENTS 4,055,412  10/1977  Wat ......................................... 71/92

OTHER PUBLICATIONS

H. T. Freebairn et al, Journal of the Air Pollution Control Association, vol. 10, No. 4, 314 (1960).
Chemical Week, 141,25, 70 (Dec. 16, 1987).
M. Windholz et al., "The Merck Index," 10th ed., entries 846 and 4973, pp. 120 and 738, Merck & Co., Inc., Rahway, N.J. (1983).
Hield et al., Chem. Abst. vol. 76 (1972), 11010y.

Primary Examiner—Richard L. Raymond
Assistant Examiner—Mark W. Russell
Attorney, Agent, or Firm—Peter C. Richardson; Paul H. Ginsburg; Gezina Holtrust

[57] ABSTRACT

Plants and trees are effectively treated with erythorbic acid or salts thereof to reduce ozone damage to their crops.

7 Claims, No Drawings

PROCESS FOR PROTECTING PLANTS AND TREES FROM OZONE DAMAGE

BACKGROUND OF THE INVENTION

This invention relates to the treatment of plants and trees with an antioxidant to reduce ozone damage to crops.

Ozone is a common air pollutant, particularly near urban areas, and the detrimental effect of ozone to plants and trees is well-known. One method of reducing ozone damage to plants is disclosed in U.S. Pat. No. 4,055,412 suggesting treatment of the plants with certain ureas. This patent reference includes data showing reduced damage to foliage of annual plants. However, the influence on crop yield is not discussed. Vitamin C has been suggested for increase of plant growth and productivity in H. T. Freebairn, Journal of th Air Pollution Control Association, Vol. 10, No. 4, 314 (1960). The high and frequent spraying levels used, however, make the disclosed method commercially unacceptable and economically impractical.

SUMMARY OF THE INVENTION

The invention relates to a process for the protection of plants or trees which comprises applying to a plant or tree an effective amount of erythorbic acid or a salt thereof.

Particularly, the invention relates to the treatment of crop plants, fruit trees and nut trees to reduce ozone damage to the crop yields of these plants and trees. More particularly, the crop plants are perennial crop plants, such as grape vines.

DETAILED DESCRIPTION OF THE INVENTION

Erythorbic acid and sodium erythorbate are used by the food and beverage industries as antioxidants and are thus readily available products. For purposes of the invention, those salts of erythorbic acid may be employed which are agriculturally acceptable such that they are not toxic under the treatment conditions. Thus, the salt of use does not have a detrimental effect on the plants or trees being treated during treatment or thereafter. Preferably, the salt is water soluble for ease of application in aqueous solution. The preferred salt is sodium erythorbate. When reference is made below to erythorbic acid, this includes sodium erythorbate and other agriculturally acceptable salts of erythorbic acid.

It was found according to the invention that the treatment with erythorbic acid at the levels and frequencies set out below does not have a beneficial effect on the yield of the first crop harvested after treatment has begun. Continued treatment, however, increases the yield of the second and subsequent crops. The invention, therefore, is particularly of use in the treatment of crop plants which are not annual plants. Advantageously, the plants are perennial plants such as grape vines. The invention is further of use in the treatment of trees, particularly those trees which bear fruits or nuts. Again, continued treatment is required to attain increased crop yields in the second and succeeding years after the first crop is harvested. Trees that can be successfully treated include orange trees and almond trees.

Erythorbic acid is applied in an effective amount such that on continued annual treatment an increase in crop yield is obtained after the first crop is harvested. In general, erythorbic acid is applied at a range of about 1.5 to about 3.5 pounds per acre although higher rates can be used. The proper rate of application depends on the particular circumstances such as the plant or tree being treated, the ozone content in the atmosphere, the amount of rain, the amount of other oxidants in the atmosphere, etc.

Erythorbic acid can be applied in the form of compositions containing adjuvants such as carriers or diluents which are inert under the conditions of treatment. Such carriers and diluents are known in agriculture for the treatment of pests, and can be in the form of dusts, water-dispersible powders, high-strength concentrates, and aqueous or organic liquid dispersions. The compositions may contain usual adjuvants such as surfactants to provide essential coverage and wetting properties, and buffering agents to enhance overall solution stability.

Erythorbic acid is conveniently applied by spraying, e.g. by ground sprays or aerial spraying. For most effective treatment, complete coverage of the plant or tree, particularly its leaves, is essential. Per month, the level of erythorbic acid applied is at least about 500 ppm, and more likely at least about 1000 ppm or 2000 ppm. Erythorbic acid sprays or dusts are applied at levels of at least about 50 gallons, and usually at least about 150 gallons, per acre.

EXAMPLE

Three formulations of sodium erythorbate were prepared containing the following in percentage by weight and having the following pH:

| Formulation | A | B | C |
| --- | --- | --- | --- |
| Sodium erythorbate | 51.6 | 78.8 | 75.4 |
| Sodium citrate, arhydrous | 13.8 | 20.8 | — |
| Citric acid, anhydrous | 34.8 | 0.4 | — |
| Sodium tripolyphosphate | — | — | 24.6 |
| pH | 5.0 | 7.0 | 8.2 |

The three formulations were dissolved in water and about 1% of the nonionic surfactant Pluronic ® F68 (polyethylene oxide with condensate of propylene oxide with propylene glycol) in concentrations of 2000 and 4000 ppm erythorbic acid resulting in six different aqueous solutions. These solutions were sprayed on twelve separate plots, six plots being sprayed weekly and six other plots biweekly. One test plot was not sprayed and another was sprayed with 0.01% aqueous solution of Pluronic ® F68. The fourteen treatments were as follows:

| Treatment Number | Treatments | Concentration (ppm) | Application Frequency |
| --- | --- | --- | --- |
| 1 | Control (dry) | — | — |
| 2 | Control (surfactant) | — | Weekly |
| 3 | Formulation "A" | 2000 | Weekly |
| 4 | | 2000 | Biweekly |
| 5 | | 4000 | Weekly |
| 6 | | 4000 | Biweekly |
| 7 | Formulation "B" | 2000 | Weekly |
| 8 | | 2000 | Biweekly |
| 9 | | 4000 | Weekly |
| 10 | | 4000 | Biweekly |
| 11 | Formulation "C" | 2000 | Weekly |
| 12 | | 2000 | Biweekly |
| 13 | | 4000 | Weekly |
| 14 | | 4000 | Biweekly |

The plots were located in a fifty year old Thompson Seedless vineyard near Reedley, California in the San Joaquin Valley. This area is exposed to atmospheric ozone levels ob 10-12 pphm during mid-May or early June through mid-September, which is the growing and harvesting season for Thompson Seedless grapes. The vineyard was divided in half, both north-south and east-west to provide four quadrants. In each quadrant, there were 28 plots, i.e., two sets of the 14 plots described above. Each plot had five vines. The above fourteen treatments were thus done 8 times.

The plots were established in May 1984 and treatments were begun in the first week of June 1984. In accordance with standard cultural practice in the area, the vineyard was sprayed three times per year with the fungicide Bayleton ®, 1-(4-chlorophenoxy)-2,3-dimethyl-1-(1H-1,2,4-triazol-1-yl)-2-butanone, for mildew control, twice with the insecticide Kryocide, sodium aluminum fluorite, for control of chewing insects and worms, and twice with dimethoate, 0,0-dimethyl S-(N-methylcarbamoylmethyl)phonsphorodithioate for control of leaf hoppers. About 36 acre-inches irrigation water per year was applied to the vicinity of each vine.

The mean yield of grapes per vine over the previous six years from 1977 to 1983 had ranged from about 13 to 20 kilos per vine. The mean production of these six years was about 16.5 kilos per vine, or about 10.25 tons per acre.

The following tables 1-3 show the fruit yields for 1984, 1985, 1986 and 1987, and the fruit quality for 1984 and 1985 determined from fruit samples taken from the five vines in each plot and subjected to standardized tests for mean berry weight, total sugars, pH and titratable acid.

Tables 1 and 2 show that the erythorbate sprayings provided no yield response in the first season, and an average of 12.4% more fruit during the second, third, and fourth years.

Table 3 shows no differences in sugar content, pH or titratable acidity due to the treatments. Mean berry size, i.e. the mean weight of 100 berries, was essentially the same for treated and non-treated vines. The higher yields without reduction in berry size or sugar content indicate that the vines were not overcropped.

TABLE 1

Weight of fruit (kg/vine) produced by treated and untreated grapevines.*

| Treatment | 1984 | 1985 | 1986 | 1987 | 3 year Av. 1985-1987 | % of Control |
|---|---|---|---|---|---|---|
| 1 Control | 18.18 | 15.28 | 16.58 | 13.29 | 15.05 | 100 |
| 2 Surfactant only | 17.75 | 14.47 | 17.38 | 12.50 | 14.78 | 98 |
| 3 "A" weekly | 16.45 | 16.10 | 20.97 | 13.92 | 17.00 | 113 |
| 4 "A" biweekly | 18.66 | 16.58 | 19.42 | 14.31 | 16.79 | 112 |
| 5 "A" weekly | 18.00 | 17.24 | 18.80 | 14.68 | 16.91 | 112 |
| 6 "A" biweekly | 19.40 | 17.28 | 19.04 | 16.02 | 17.45 | 116 |
| 7 "B" weekly | 18.54 | 17.04 | 18.44 | 13.83 | 16.44 | 109 |
| 8 "B" biweekly | 17.74 | 16.77 | 17.34 | 15.12 | 16.41 | 109 |
| 9 "B" weekly | 16.75 | 16.04 | 17.80 | 14.07 | 15.97 | 106 |
| 10 "B" biweekly | 17.64 | 15.41 | 18.49 | 14.50 | 16.13 | 107 |
| 11 "C" weekly | 18.45 | 18.04 | 19.43 | 15.57 | 17.68 | 117 |
| 12 "C" biweekly | 18.10 | 16.87 | 18.06 | 14.74 | 16.56 | 110 |
| 13 "C" weekly | 17.14 | 16.34 | 18.48 | 15.07 | 16.63 | 110 |
| 14 "C" biweekly | 18.16 | 16.86 | 20.00 | 15.59 | 17.48 | 116 |

*All values represent the average of eight plots (five vines each).

TABLE 2

Fruit production (kg/vine) by Thompson Seedless grapes as influenced by various factors.

| Factor | 1984 | 1985 | 1986 | 1987 | 3 year Av. 1985-1987 |
|---|---|---|---|---|---|
| Treated vs. Untreated | | | | | |
| Non-treated | 17.96 | 14.87 | 16.98 | 12.90 | 14.92 |
| All Treated | 17.92 | 16.71 | 18.86 | 14.78 | 16.78 |
| Formulation | | | | | |
| "A" - Acid | 18.12 | 16.80 | 19.56 | 14.74 | 17.03 |
| "B" - Neutral | 17.67 | 16.32 | 18.02 | 14.38 | 16.24 |
| "C" - Basic | 17.96 | 17.02 | 18.99 | 15.24 | 17.08 |
| Concentration | | | | | |
| 2000 ppm (low) | 17.99 | 16.90 | 18.95 | 15.83 | 17.23 |
| 4000 ppm (high) | 17.84 | 16.53 | 18.77 | 14.58 | 16.62 |
| Frequency of Application | | | | | |
| Weekly | 17.55 | 16.80 | 18.99 | 14.52 | 16.77 |
| Biweekly | 18.28 | 16.63 | 18.73 | 15.04 | 16.80 |

TABLE 3

Fruit quality of Thompson Seedless grapes from treated and non-treated vines.

| Quality Criteria | 1984 Treated | 1984 Non-treated | 1985 Treated | 1985 Non-treated |
|---|---|---|---|---|
| Mean berry wt. (g) | 1.66 | 1.60 | 1.56 | 1.60 |
| Brix (% sugar) | 20.2 | 20.3 | 20.0 | 20.1 |
| pH | 3.76 | 3.75 | 3.58 | 3.61 |
| Titratable acidity | .443 | .453 | .490 | .490 |

I claim:

1. A process for protecting grape vines to reduce ozone damage to crop yields which comprises applying to a grape vine an effective amount of erythorbic acid or a salt thereof during a period of time continuing after harvesting of the first crop to which said erythorbic acid or a salt thereof has been applied for protection of a crop harvested after said first crop.

2. A process according to claim 1 wherein said salt is sodium erythorbate.

3. A process according to claim 1 wherein said application is by spraying.

4. A process according to claim 1 wherein said erythorbic acid or salt thereof is applied in an aqueous solution.

5. A process for protecting grape vines to reduce ozone damage to crop yields which comprises applying to a grape vine an amount of about 500 ppm to 4000 ppm of erythorbic acid or a salt thereof during a period of time continuing after harvesting of the first crop to which said erythorbic acid or a salt thereof has been applied for protection of a crop harvested after said first crop.

6. A process according to claim 8 wherein said amount ranges from about 1000 ppm to 2000 ppm.

7. A process according to claim 5 wherein said salt is sodium erythorbate.

* * * * *